United States Patent
Pollack

(10) Patent No.: US 7,087,095 B2
(45) Date of Patent: Aug. 8, 2006

(54) HAIR COLORING COMPOSITION AND METHOD

(75) Inventor: George Pollack, Fair Lawn, NJ (US)

(73) Assignee: HairMarker LLC, Santa Fe, NM (US)

( * ) Notice: Subject to any disclaimer, the term of this patent is extended or adjusted under 35 U.S.C. 154(b) by 928 days.

(21) Appl. No.: 10/215,303

(22) Filed: Aug. 6, 2002

(65) Prior Publication Data

US 2004/0025264 A1 Feb. 12, 2004

(51) Int. Cl.
*A61K 7/13* (2006.01)

(52) U.S. Cl. .................. 8/405; 8/455; 8/463; 8/486; 8/512; 8/514; 8/552; 8/553; 8/581

(58) Field of Classification Search ............... 8/405, 8/455, 463, 486, 512, 514, 552, 553, 581
See application file for complete search history.

(56) References Cited

U.S. PATENT DOCUMENTS 6,379,400 B1 * 4/2002 Braun et al. ............... 8/415

* cited by examiner

*Primary Examiner*—Yogendra N. Gupta
*Assistant Examiner*—Eisa Elhilo
(74) *Attorney, Agent, or Firm*—Buchanan Ingersoll PC

(57) ABSTRACT

A hair dye composition that is particularly applicable by localized capillary action, and comprises one or more FD&C and D&C dyes, water, alcohol, Polectron 430, and a polymeric ruboff protector component for preventing ruboff of the color of the dye.

7 Claims, No Drawings

HAIR COLORING COMPOSITION AND METHOD

FIELD OF INVENTION

The present invention relates to a hair dye composition and a process for its use on hair.

BACKGROUND

Many compositions for dyeing human hair are known. These are applied directly to the hair by, for example, squeezing dye liquid through a nozzle, or spraying a dye composition, or applying the dye by any other conventional method. Often hair dyeing involves applying a dye composition and fixing it by oxidation using peroxide or the like.

U.S. Pat. No. 5,964,226 to Joan Lasker Sobel (which is incorporated herein by reference thereto) describes a unique hair product application system wherein hair coloring composition is maintained in a reservoir provided with an applicator tip extending from within the inside of the reservoir to absorb hair coloring solution and to deliver it to the outside of the reservoir by capillary action to an applicator tip for applying the coloring solution to the hair to be treated.

The present hair coloring composition is useful in the dispensers of the type disclosed in the aforesaid hair product applicator of U.S. Pat. No. 5,964,226 and to meet its unique requirements, but can also be applied in other ways particularly for touching up the roots of growing hair which was previously dyed with a permanent (e.g., oxidative hair dye), for highlighting hair, and for coloring sections of hair.

BRIEF DESCRIPTION OF THE INVENTION

The hair dyeing composition of the present invention comprises a generally anionic, or solvent-type temporary dye. They are generally acid dyes or solvent dyes. Generally the various FD&C and D&C dyes fall into this category of dyes that are useful in accordance with the present invention. The dyes that are useful in accordance with the present invention, are all categorized in the Color Index under their own C.I. numbers. Particularly suitable dyes are capable of capillary flow when in solution. Such dyes typically are generally free of or contain a low concentration of foaming agents such as surfactants or detergents. They suitably have a controlled, nearly free-flowing viscosity, such as in the range of from about 10 to about 200 cps to be nearly but not quite free flowing and yet not drip or cause a buildup on the hair. The dye composition is soluble both in water and in alcohol, and is dissolved in a liquid vehicle which has a controlled vapor pressure for a predetermined rate of evaporation, i.e. a controlled rate of drying. The dye compositions of the present invention can optionally also contain a clear polymeric dye-shield anti-ruboff component to prevent the transfer of the applied color from the hair to surfaces such as pillows, clothes, etc., such as a polymer of vinyl acetate and of vinyl pyrrolidone, or a copolymer thereof which has been found to be particularly effective for that purpose.

DETAILED DESCRIPTION

The novel hair dyeing compositions of the present invention comprise one or more FD&C and/or D&C dyes in individual concentrations of 0.10 to 3.0% wt. based on the composition, or in some cases and in the case of less intensive colors up to about 5% wt. The composition suitably contains up to about 0.20% wt. of a conditioning wheat protein, sold by the Croda Company under the trade designation Tritisol, and to about 0.1% of a shine-contributing silicone, such as the silicone sold by Dow Coming Corp. under the trade designation Silicon 193 (dimethicon copolyol), and up to about 5.0% wt. of propylene glycol, with suitably 49.9 to 51.7% wt. deionized water, and up to about 20% wt. ethyl alcohol. The Tritisol hydrolyzed wheat protein is a nonionic compound and does not interfere with the nonionic dyes, and does not cause any precipitation.

The Polectron 430 copolymer emulsion can be suitably employed at a concentration of between 10% wt. to 50% wt., most suitably about 20% wt. It produces more vivid colors with the special dyes of the present invention, and delivers a truer result.

The composition of the present invention must meet various requirements to be suitable for use in a hair dye applicator with a capillary flow or other type of applicator which applies it to the hair through direct contact therewith, for coloring hair roots, highlighting and section coloring of hair. That coloring ability derives partly from the low viscosity (<100 cps) of the herein compositions. The method of the present invention involves applying the hair dye composition by a localized application by the present invention through an applicator to the hair, wherein the material of the applicator tip hair contacting surface is substantially saturated with the semipermanent hair dye composition of the present invention. The applicator can be that of the aforesaid U.S. Pat. No. 5,964,226, or a sponge or a wad of cotton or an absorbent dipstick or pen-type applicator.

In accordance with the present invention, the dyes are FD&C and D&C dyes, however, they do not adhere to hair by any ionic mechanism. The composition of the present invention must flow through the applicator without clogging it. It should be capable of instantaneous application upon touching the hair and it must not drip. The dyes should be capable of penetrating the cuticle of the hair in a level fashion without leaving an undesirable coating. It should suitably be non-foaming and should be at least somewhat quick drying. The composition should have a sufficiently, low viscosity so that the composition flows easily from the applicator to the hair surfaces contacted thereby, and should have a suitable acid pH to allow the desired degree permanence on the hair.

A principal feature of the present invention is the nature of the FD&C and D&C dyes which has not been used heretofore for hair coloring. Suitable dyes are generally water and alcohol soluble and are safe for use on human hair. There are many dyes that tend not to flow through a wick and capillary applicator and tend to clog the system. The ratio of water and alcohol or other volatile solvent can be varied in the vehicle of the hair dye composition to obtain a predetermined rate of evaporation thereof. The total solvent (e.g. water plus volatile solvent) can be up to 80% (wt) of the dye composition to leave some room for the up to 20% Polectron 430 polymer additive. Butyl cellosolve or alcohol proportion in the vehicle can be varied up to 50% of the solvent, with a lower percentage being preferred, with a proportionally lower concentration of water, when a higher rate of evaporation is desired. The appropriate proportions of water and the more volatile solvent can be determined by routine experimentation to obtain the desired evaporation rate.

Particularly suitable dyes include one or more FD&C and D&C dyes. These dyes are suitably used by themselves or mixed with other FD&C and D&C dyes. These dyes require no preliminary patch test, and are more vivid and deliver truer colors to hair. However, if the addition of any other type of hair dye is desired, then a patch test need to be carried out on a skin patch for 48 hours prior to use.

The dyes are moreover capable of being instantly deposited on the hair. They allow for repeated touching to the hair with increased coverage upon each application. They penetrate the hair shaft leaving a clean, non-messy level of color molecules on the hair. No unsightly mess is left on the hair or scalp on drying.

The compositions of the present invention can suitably contain a vinylpyrrolidone/styrene copolymer nonionic emulsion, such as sold under the trademark Polectron 430 by International Specialty Products, Inc. This is a fluid, milky white emulsion with a solids content of about 40% wt. Its solids content has a particle size under 0.5 microns, It assists in the even distribution and prolonged suspension and improved stability of the colors, contributes to a more even flow of colors and their application.

Level application can be promoted by the use of an alcohol solvent system, e.g., ethyl alcohol, isopropyl alcohol or a butyl alcohol.

Quick drying with a safe and clean solvent was realized with an alcoholic system such as with ethyl alcohol. It has a pleasant odor and works with water to evaporate at a faster rate than water alone. Isopropyl alcohol can also be used but it has a less desirable odor. Butyl alcohol, such as a tert butyl alcohol butylene glycol, 2-butanol, or butoxy ethanol (butyl cellosolve) is also suitable as solvents for direct dyes and to improve penetration into the hair shaft.

An optional protective ruboff shield component provides against ruboff of the color to objects coming into contact with dyed hair, e.g., pillow cases, clothing, etc. The polymeric ruboff shield should not interfere with the coloring process. The polymer used in the present composition is compatible with the hair while forming a ruboff shield that surrounds each hair shaft and is gradually removed upon each subsequent shampooing. Polyvinylpyrrolidone alone or copolymers of vinyl acetate and vinylpyrrolidone monomers, or mixtures, such as is sold by International Specialty Chemicals, Corp. under the trade designation PVP/VA E635, are particularly effective to serve this purpose, because they are not tacky and do not interfere with the free capillary flow of the dye liquids. Generally 50% solutions of these copolymers are sold by International Specialty Products Corp., and by BASF. Most or all non-ionic polymers are likely to work, and many others can be identified by routine experimentation.

The viscosity of the composition to be used is important to be free-flowing and yet not drip or cause a build-up on the hair. Systems using standard thickening agents such as gums are not successful. However, a slight amount of a thickener such as a carbomer or a cellulose can be used especially to prevent a too rapid runoff from the applicator. A viscosity in the range of 10–200 cps, has been found to meet these requirements, more suitably between 10 and 100 cps to be sufficiently flowing.

It has been found that the composition for hair coloring should be at a pH from about 6 to about 6.5 for best coloring of the hair, however, the most suitable pH will also depend on the identity of the dye and its host substantivity, as will be readily known to the skilled hair colorist.

The following example further illustrates the present invention and embodiments thereof. All parts and percentages are by weight unless otherwise indicated.

EXAMPLE

All parts and percentages in the examples and throughout the application are by weight.

A suitable composition of the present invention is represented in this example.

| Phase A | | |
|---|---|---|
| Deionized water | 49.9–51.7 | |
| PVP/VA E 365 | 2.0 | |
| Tritisol (Croda) | 0.20 | |
| Dow Corning Silicone 193 (for shine) | 0.1 | (Dimethicone copolyol) |
| Propylene glycol | 5.0 | |
| Ethyl alcohol | 20.00 | |
| Phase B (choice of one or more dyes) | | |
| FD & C Red 4 | 0.1–0.3 | |
| FD & C Red 28 | 0.1–3.0 | |
| FD & C Red 40 | 0.1–3.0 | |
| D & C Green 5 | 0.1–3.0 | |
| FD & C Green 3 | 0.1–3.0 | |
| D & C Green 8 | 0.1–3.0 | |
| FD & C Yellow 10 | 0.1–5.0 | |
| D & C Orange 4 | 0.1–3.0 | |
| Phase C | | |
| Polectron 430 | 20.00 | |

The composition is prepared from the ingredients by adding the deionized water to a stainless steel kettle, then adding the PVP/VA copolymer and mix until clear, because the polymer has completely dissolved. Then add the Tritisol, Silicone 193, propylene glycol, and ethyl alcohol, and stir until clear.

Next add the dyes to the previously prepared mixture, and mix until dyes are completely dissolved and no pieces remain, finally add the Polectron 430 and mix until the color solution is completely uniformly milky. Check, and if needed, adjust shade for final color.

I claim:

1. A hair dye composition for localized application to hair, by capillary action, which comprises one or more acid dyes or solvent dyes, water, alcohol, vinylpyrrolidone/styrene copolymer nonionic emulsion, and a polymeric ruboff protector component for preventing ruboff of the color of the dye.

2. The hair dye composition of claim 1, wherein said polymeric ruboff protector components is a copolymer of vinyl acetate and vinylpyrrolidone.

3. The hair dye composition of claim 1, wherein the concentration of vinylpyrrolidone/styrene copolymer nonionic emulsion, is up to 20% wt.

4. The hair dye composition of claim 1, wherein the concentration of said alcohol and water is up to 80% wt.

5. The hair dye composition of claim 1, wherein the pH of the composition is an acid pH.

6. The hair dye composition of claim 1, wherein the pH of the composition is between pH 6 and 6.5.

7. The hair dye composition of claim 1, further comprising a conditioning wheat protein and dimethicon copolyol.

* * * * *